US011229381B2

(12) United States Patent
Kurachi et al.

(10) Patent No.: US 11,229,381 B2
(45) Date of Patent: Jan. 25, 2022

(54) SEMICONDUCTOR INTEGRATED CIRCUIT AND RESPIRATORY MOTION TESTING APPARATUS

(71) Applicant: SOCIONEXT INC., Kanagawa (JP)

(72) Inventors: Ryusuke Kurachi, Yokohama (JP);
Hiroyuki Tomura, Yokohama (JP);
Masato Yoshioka, Yokohama (JP);
Masaya Tamamura, Yokohama (JP);
Amane Inoue, Yokohama (JP)

(73) Assignee: SOCIONEXT INC., Yokohama (JP)

( * ) Notice: Subject to any disclaimer, the term of this patent is extended or adjusted under 35 U.S.C. 154(b) by 289 days.

(21) Appl. No.: 16/164,386

(22) Filed: Oct. 18, 2018

(65) Prior Publication Data

US 2019/0117122 A1 Apr. 25, 2019

(30) Foreign Application Priority Data

Oct. 19, 2017 (JP) .............................. JP2017-202607

(51) Int. Cl.
*A61B 5/113* (2006.01)
*A61B 5/11* (2006.01)
(Continued)

(52) U.S. Cl.
CPC ............ *A61B 5/113* (2013.01); *A61B 5/0809* (2013.01); *A61B 5/1126* (2013.01); *H03K 3/037* (2013.01); *A61B 5/08* (2013.01); *A61B 5/1135* (2013.01)

(58) Field of Classification Search
CPC ..... A61B 5/0809; A61B 5/113; A61B 5/1135; A61B 5/0816; A61B 5/053; A61B 5/0535; A61B 5/1126; H03K 3/02; H03K 3/037
See application file for complete search history.

(56) References Cited

U.S. PATENT DOCUMENTS 4,305,400 A 12/1981 Logan
4,708,146 A * 11/1987 Lane .................... A61B 5/0809
324/709

(Continued)

FOREIGN PATENT DOCUMENTS

JP S59-2306 U 1/1984
JP H03-33607 U 4/1991
(Continued)

*Primary Examiner* — Sean P Dougherty
*Assistant Examiner* — Kyle W. Kretzer
(74) *Attorney, Agent, or Firm* — Arent Fox LLP (57) ABSTRACT

A pulse signal generator circuit generates first and second pulse signals for electrodes placed on the chest of a subject with phases that differ by 180°. A rectifier circuit receives a potential difference signal, which reflects an impedance between the electrodes that changes according to respiratory motion and in which timing of changes caused by changes in the first pulse signal or the second pulse signal is delayed from the timing of the changes in the first pulse signal and the second pulse signal, and outputs a rectified signal produced by rectifying the potential difference signal. A control signal generator circuit causes the rectifier circuit to invert the potential difference signal, which becomes a negative voltage value from the certain timing, to a positive voltage value from the certain timing. An AD converter circuit outputs a digital value based on the magnitude of the rectified signal.

3 Claims, 9 Drawing Sheets

(51) Int. Cl.
*H03K 3/037* (2006.01)
*A61B 5/08* (2006.01)

(56) References Cited

U.S. PATENT DOCUMENTS

| | | | |
|---|---|---|---|
| 5,170,794 A | 12/1992 | Reiche | |
| 5,623,938 A * | 4/1997 | Addiss | A61B 5/0809 |
| | | | 128/204.18 |
| 5,749,369 A * | 5/1998 | Rabinovich | A61B 5/0535 |
| | | | 600/372 |
| 6,616,608 B2 | 9/2003 | Honda et al. | |
| 7,917,204 B2 * | 3/2011 | Olson | A61B 5/053 |
| | | | 600/547 |
| 9,980,664 B2 | 5/2018 | Fernando et al. | |
| 2007/0208232 A1 * | 9/2007 | Kovacs | A61B 5/6831 |
| | | | 600/300 |
| 2013/0281875 A1 * | 10/2013 | Narasimhan | A61B 5/0816 |
| | | | 600/536 |
| 2014/0309540 A1 * | 10/2014 | Morikawa | A61B 5/0826 |
| | | | 600/484 |

FOREIGN PATENT DOCUMENTS

| | | |
|---|---|---|
| JP | H04-122239 A | 4/1992 |
| JP | 2001-190510 A | 7/2001 |
| WO | WO 2014/006891 A1 | 1/2014 |
| WO | WO 2014/147939 A1 | 9/2014 |

\* cited by examiner

SEMICONDUCTOR INTEGRATED CIRCUIT AND RESPIRATORY MOTION TESTING APPARATUS

CROSS-REFERENCE TO RELATED APPLICATION

This application is based upon and claims the benefit of priority of the prior Japanese Patent Application No. 2017-202607, filed on Oct. 19, 2017, the entire contents of which are incorporated herein by reference.

FIELD

The embodiments discussed herein are related to a semiconductor integrated circuit and a respiratory motion testing apparatus.

BACKGROUND

Impedance pneumography is one example of a method used to test human respiratory motion. Impedance pneumography uses a plurality of electrodes placed on the subject's chest to apply a constant current to the subject's body and measures the impedance of the body, which will vary as the amount of oxygen in the lungs changes due to respiratory motion, based on changes in the voltage between the electrodes. Note that to avoid having an adverse effect on the body, impedance pneumography uses a weak alternating current (hereinafter "AC") signal.

There has been a trend in recent years for medical devices to become smaller. See, for example, the following documents.

International Publication Pamphlet No. WO2014/147939
Japanese Laid-open Patent Publication No. 2001-190510

As the AC signal used in impedance pneumography, it would be conceivable to use a positive pulse signal that can be provided by a single-supply circuit which occupies a comparatively small area compared to a power supply for a sinusoidal wave signal. To also perform measurement during the 0V period, a pulse signal with a phase difference of 180° is used, and then the potential difference of the waveform after full-wave rectification is subjected to AD (Analog to Digital) conversion.

With this configuration however, due to the influence of the delay from the supplying of the positive pulse signal to the two electrodes until the potential difference is detected by the testing apparatus, there is the risk that rectification will not be performed correctly, resulting in measurement errors for the impedance. When this happens, it is not possible to accurately test the respiratory movements. It is therefore important to avoid measurement errors for impedance.

SUMMARY

According to one aspect, there is provided a semiconductor integrated circuit including: a pulse signal generator circuit configured to generate a first pulse signal, which is supplied to a first electrode out of the first electrode and a second electrode placed on a chest of a subject, and a second pulse signal, which is supplied to the second electrode, a phase of the second pulse signal differing by 180° to a phase of the first pulse signal; a rectifier circuit configured to receive a potential difference signal and output a rectified signal produced by rectifying the potential difference signal, the potential difference signal being a signal in which an impedance between the first electrode and the second electrode is reflected, the impedance between the first electrode and the second electrode changing according to respiratory motion of the subject, first timing of a change of the potential difference signal caused by the first pulse signal or the second pulse signal changing being delayed by a first time from second timing at which the first pulse signal or the second pulse signal changes; a control signal generator circuit configured to supply a first control signal, the first control signal causing the rectifier circuit to invert the potential difference signal, which becomes a negative voltage value from the first timing, to a positive voltage value from the first timing; and an AD converter circuit configured to output a digital value based on a magnitude of the rectified signal.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Several embodiments will be described below with reference to the accompanying drawings, wherein like reference numerals refer to like elements throughout.

First Embodiment

Figure 1:
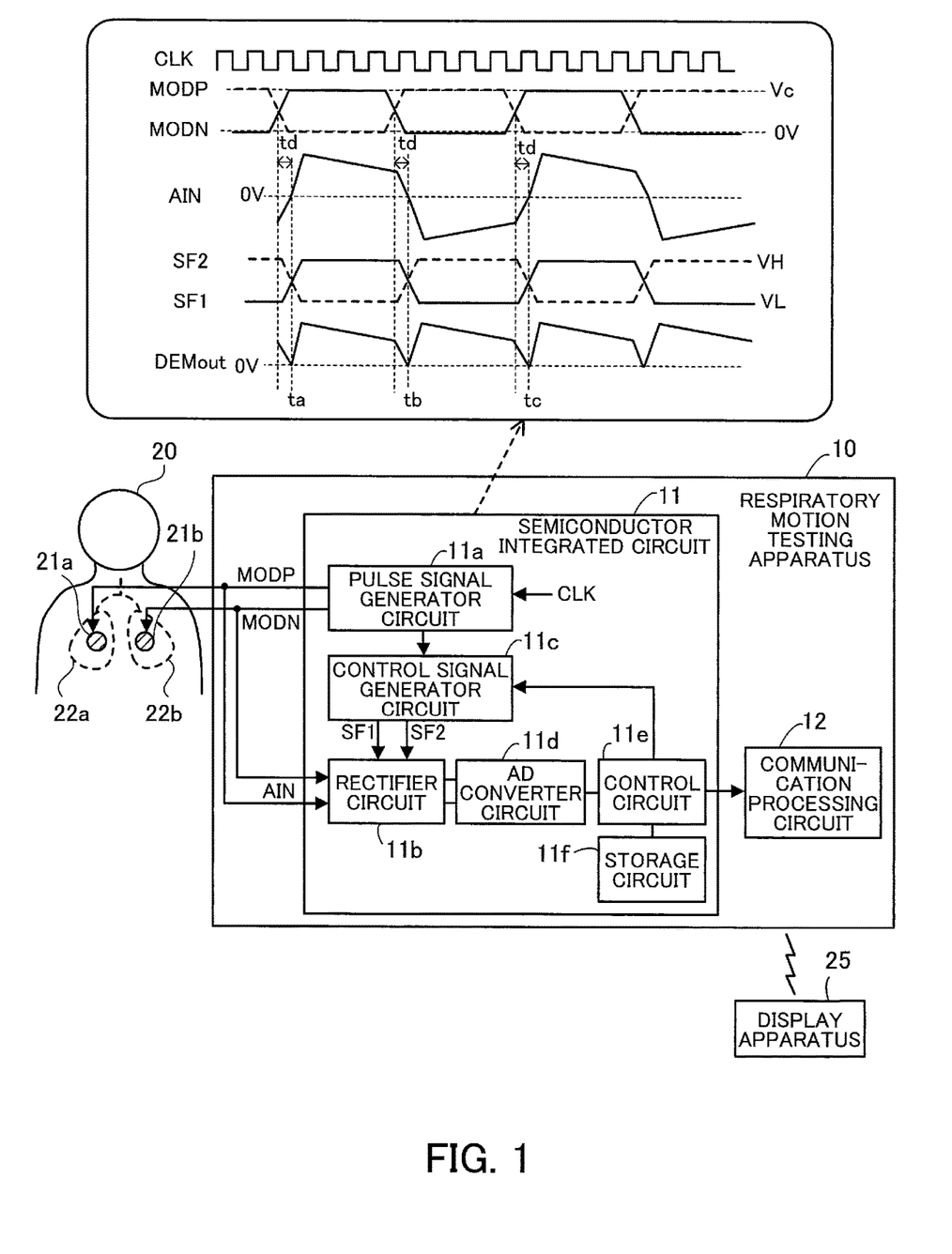
FIG. 1 depicts examples of a respiratory motion testing apparatus and a semiconductor integrated circuit according to a first embodiment.

FIG. 1 depicts examples of a respiratory motion testing apparatus and a semiconductor integrated circuit according to a first embodiment.

A respiratory motion testing apparatus 10 applies a voltage across electrodes 21a and 21b placed on the chest of a subject 20 to cause a current to flow across the chest and measures the impedance of the body, which will vary as the amount of oxygen in the lungs 22a and 22b changes, based on changes in the voltage between the electrodes 21a and 21b.

The respiratory motion testing apparatus 10 includes a semiconductor integrated circuit 11 and a communication processing circuit 12.

As one example, the semiconductor integrated circuit 11 is a single-chip LSI (Large Scale Integrated circuit) and includes a pulse signal generator circuit 11a, a rectifier circuit 11b, a control signal generator circuit 11c, an AD converter circuit 11d, a control circuit 11e, and a storage circuit 11f.

The pulse signal generator circuit 11a generates a pulse signal MODP that is supplied to an electrode 21a and a pulse signal MODN that is supplied to the electrode 21b. The pulse signal MODN is a signal whose phase is 180° different to the pulse signal MODP. The pulse signals MODP and MODN are generated for example by frequency-dividing a clock signal CLK. As one example, assume that the frequency of the clock signal CLK is 12 MHz and the frequency of the pulse signals MODP and MODN is 32 KHz.

Note that although the clock source that generates the clock signal CLK is omitted from FIG. 1, the clock source may be provided inside the semiconductor integrated circuit 11 or may be provided outside the semiconductor integrated circuit 11 but inside the respiratory motion testing apparatus 10.

The rectifier circuit 11b receives a potential difference signal AIN indicating a potential difference between the electrodes 21a and 21b and outputs a rectified signal generated by rectifying the potential difference signal AIN. Note that the timing at which the potential difference signal AIN changes due to changes in the pulse signals MODP and MODN is delayed compared to the timing of changes in the pulse signals MODP and MODN. The reasons for this are described later.

Figure 2:
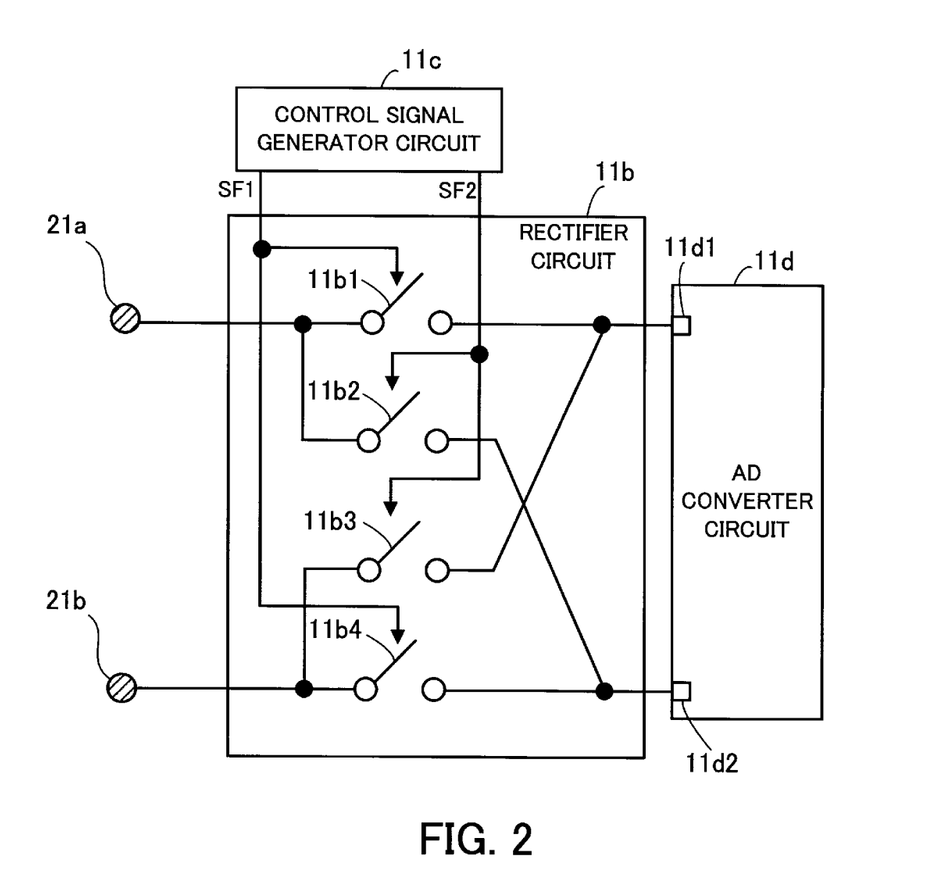
FIG. 2 depicts one example of a rectifier circuit.

FIG. 2 depicts one example of a rectifier circuit.

The rectifier circuit 11b includes switches 11b1, 11b2, 11b3, and 11b4. One end of the switch 11b1 is connected to the electrode 21a and the other end of the switch 11b1 is connected to a terminal 11d1 of the AD converter circuit 11d. One end of the switch 11b2 is also connected to the electrode 21a and the other end of the switch 11b2 is connected to a terminal 11d2 of the AD converter circuit 11d. One end of the switch 11b3 is connected to the electrode 21b and the other end of the switch 11b3 is connected to the terminal 11d1 of the AD converter circuit 11d. One end of the switch 11b4 is also connected to the electrode 21b and the other end of the switch 11b4 is connected to the terminal 11d2 of the AD converter circuit 11d.

The control signal generator circuit 11c outputs two control signals SF1 and SF2. The switches 11b1 and 11b4 are turned on and off by the control signal SF1 and the switches 11b2 and 11b3 are turned on and off by the control signal SF2.

As one example, the switches 11b1 to 11b4 are realized by MOSFETs (Metal-Oxide-Semiconductor Field-Effect Transistors). With this configuration, the control signals SF1 and SF2 are supplied to the gate electrodes of the MOSFETs and the MOSFETs are set in an on state or an off state in keeping with the voltage of the control signals SF1 and SF2.

The description will now return to FIG. 1.

The control signal generator circuit 11c outputs the control signals SF1 and SF2 that control the rectifier circuit 11b. The control signal SF2 is a signal whose phase differs to the control signal SF1 by 180°. As one example, the control signals SF1 and SF2 are signals with different phases produced by delaying the pulse signals MODP and MODN by predetermined delays.

The potential difference signal AIN may become a negative voltage value starting from timing which is the delay described above after timing at which the pulse signals MODP and MODN change. However, by using the control signals SF1 and SF2, the control signal generator circuit 11c causes the rectifier circuit 11b to invert the potential difference signal AIN to a positive voltage value starting from the timing at which the potential difference signal AIN becomes a negative voltage value.

The AD converter circuit 11d performs AD conversion and outputs a digital value based on the magnitude of the rectified signal. Note that the AD converter circuit 11d may convert a rectified signal that has been amplified by an amplifier, not illustrated, to a digital value.

The control circuit 11e calculates the impedance based on the digital value outputted by the AD converter circuit 11d. The control circuit 11e may also calculate a respiratory volume based on the calculated impedance, for example by using a relational expression for impedance and respiratory volume stored in advance in the storage circuit 11f. The control circuit 11e may alternatively calculate the respiratory volume directly from the digital value outputted by the AD converter circuit 11d. The control circuit 11e may also supply a signal that controls the timing at which the control signals SF1 and SF2 change to the control signal generator circuit 11c. The delay described above fluctuates according to a variety of conditions, such as the types of the electrodes 21a and 21b, the lengths and types of the cables that connect the electrodes 21a and 21b and the respiratory motion testing apparatus 10, and the circuit configuration of the semiconductor integrated circuit 11. In accordance with the changes in the above delay due to testing conditions like those mentioned here, the control circuit 11e controls the timing at which the control signals SF1 and SF2 change so that the potential difference signal AIN described above is inverted to a positive voltage starting from the timing at which the potential difference signal AIN becomes a negative value.

As examples, the control circuit 11e is a processor such as a CPU (Central Processing Unit) or a DSP (Digital Signal Processor) or may be a group of a plurality of processors (sometimes referred to as a "multiprocessor"). The control circuit 11e may include an electronic circuit for a dedicated application, such as an ASIC (Application Specific Integrated Circuit) or an FPGA (Field Programmable Gate Array). The control circuit 11e uses various data stored in the storage circuit 11f to execute a program stored in the storage circuit 11f.

As examples, the storage circuit 11f includes a volatile storage apparatus such as a RAM (Random Access Memory) or a nonvolatile storage apparatus such as a flash memory or an EEPROM (Electrically Erasable Programmable Read Only Memory). As one example, a program stored in a nonvolatile storage apparatus is expanded in a volatile storage apparatus and executed based on control by the control circuit 11e. As examples, the program includes a process that calculates impedance (or respiratory volume) from the digital value, a process that controls the timing at which the control signals SF1 and SF2 change, and a process that controls the communication processing circuit 12.

The communication processing circuit 12 transmits and receives information via wired or wireless communication to and from an apparatus outside the respiratory motion testing apparatus 10. FIG. 1 depicts how the communication processing circuit 12 transmits information by wireless communication to a display apparatus 25 (for example, a tablet terminal). The communication processing circuit 12 transmits information (that is, the impedance or the respiratory volume) based on the digital value outputted by the AD converter circuit 11d.

Before describing the operation of the respiratory motion testing apparatus 10 and the semiconductor integrated circuit 11 according to the first embodiment, an example operation where the timing of changes in the pulse signals MODP and MODN and the potential difference signal AIN are the same (that is, a case where there is no delay) will be described.

Figure 3:
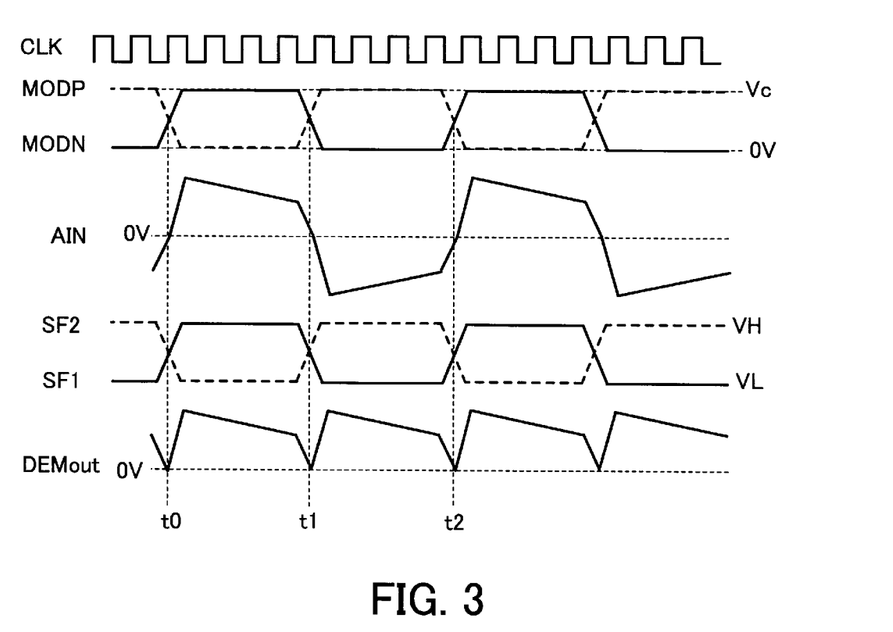
FIG. 3 is a timing chart depicting examples of signal waveforms of respective elements when there is no delay.

FIG. 3 is a timing chart depicting examples of signal waveforms of the respective elements when there is no delay. In FIG. 3, examples of changes over time in the clock signal CLK, the pulse signals MODP and MODN, the potential difference signal AIN, the control signals SF1 and SF2, and a rectified signal DEMout outputted by the rectifier circuit 11b are depicted.

At timing t0, t1, and t2 where the pulse signals MODP and MODN rise from 0V to a predetermined voltage Vc or fall from the voltage Vc to 0V, the potential difference signal AIN changes from a positive voltage value to a negative voltage value or from a negative voltage value to a positive voltage value.

Note that changes in impedance that accompany respiratory motion appear in the potential difference signal AIN. As one example, the voltage value of the potential difference signal AIN gradually falls during a period from timing t0 to timing t1.

As described above, when the timing of changes in the pulse signals MODP and MODN and in the potential difference signal AIN are the same, the timing at which the control signals SF1 and SF2 are changed may be matched to the timing of changes in the pulse signals MODP and MODN.

As one example, at timing t0, the control signal generator circuit 11c raises the control signal SF1 to a voltage VH that turns on the switches 11b1 and 11b4 depicted in FIG. 2 and lowers the control signal SF2 to a voltage VL that turns off the switches 11b2 and 11b3. As a result of this, the rectifier circuit 11b outputs the rectified signal DEMout that is the same as the positive potential difference signal AIN during the period from timing t0 to timing t1. Note that as examples, the voltage VH is a power supply voltage and the voltage VL is 0V.

At timing t1, the control signal generator circuit 11c lowers the control signal SF1 to the voltage VL that turns off the switches 11b1 and 11b4 and raises the control signal SF2 to the voltage VH that turns on the switches 11b2 and 11b3. As a result of this, the rectifier circuit 11b outputs the rectified signal DEMout produced by inverting the potential difference signal AIN that is a negative voltage value to a positive voltage value during the period from timing t1 to timing t2.

In reality however, the timing of changes in the potential difference signal AIN that are caused by changes in the pulse signals MODP and MODN are delayed with respect to the timing of changes in the pulse signals MODP and MODN. This is due to the influence of propagation delays of signals in the human body and propagation delays due to the paths (cable lengths or the like) between the electrodes 21a and 21b and the rectifier circuit 11b.

Figure 4:
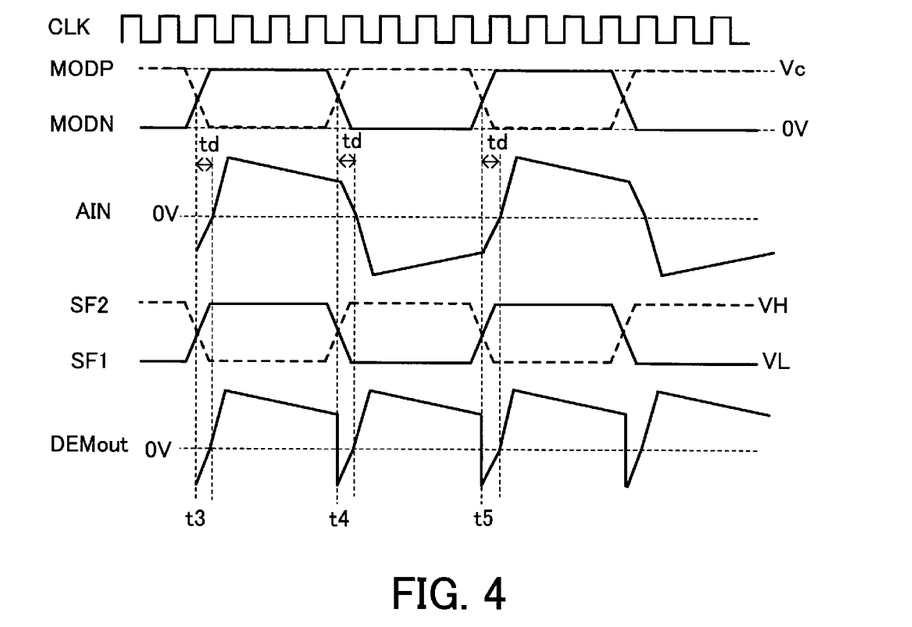
FIG. 4 is a timing chart depicting examples of signal waveforms of respective elements when there is a delay.

FIG. 4 is a timing chart depicting examples of signal waveforms of the respective elements when there is a delay.

At timing t3, t4, and t5 where the pulse signals MODP and MODN rise from 0V to the voltage Vc or fall from the voltage Vc to 0V, the potential difference signal AIN changes from a positive voltage value to a negative voltage value or from a negative voltage value to a positive voltage value with a delay.

When the timing of changes in the control signals SF1 and SF2 is kept the same as the timing of changes in the pulse signals MODP and MODN, as depicted in FIG. 4, a period where the rectified signal DEMout outputted by the rectifier circuit 11b is a negative voltage value is produced. That is, rectification is not performed properly.

In this case, errors occur in the digital value after AD conversion, so that measurement errors are produced for the impedance. This means that it is not possible to accurately test respiratory movements.

To solve this problem, in the semiconductor integrated circuit 11 according to the first embodiment, the control signal generator circuit 11c causes the rectifier circuit 11b to invert the potential difference signal AIN between positive and negative at timing that takes the delay described above into account.

As depicted in an upper part of FIG. 1, the control signal generator circuit 11c changes the control signals SF1 and SF2 to the voltage VH or the voltage VL at timing ta, tb, and tc where a time td has passed from the timing of the changes in the pulse signals MODP and MODN. As a result, as one example, the rectifier circuit 11b outputs the rectified signal DEMout produced by inverting the potential difference signal AIN to a positive voltage value from timing tb at which the potential difference signal AIN becomes a negative voltage value.

By performing these processes, the period where the rectified signal DEMout becomes a negative voltage value is eradicated, indicating that rectification is properly performed. By doing so, measurement errors for impedance are avoided. Accordingly, it is possible to accurately test respiratory movements.

The rectified signal DEMout of the rectifier circuit 11b depicted in FIG. 1 is converted to a digital value by the AD converter circuit 11d. As one example, the control circuit 11e calculates the impedance from this digital value and further calculates the respiratory volume. Information on the respiratory volume is transmitted from the communication processing circuit 12 to the display apparatus 25 based on control by the control circuit 11e.

Note that it is also possible for the respiratory motion testing apparatus 10 depicted in FIG. 1 to acquire an electrocardiogram based on the potential difference between the electrodes 21a and 21b in a period where the pulse signals MODP and MODN are not supplied to the electrodes 21a and 21b. The respiratory motion testing apparatus 10 may also acquire an electrocardiogram using a plurality of other electrodes aside from the electrodes 21a and 21b. The respiratory motion testing apparatus 10 may then transmit information on the acquired electrocardiogram to the display apparatus 25.

Figure 5:
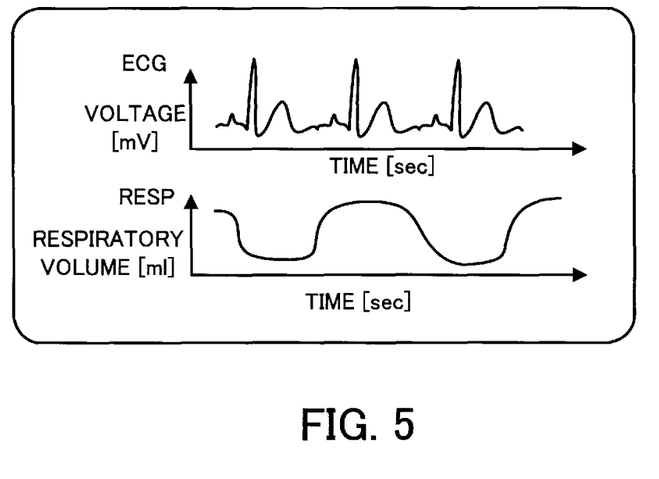
FIG. 5 depicts one example of a respiratory waveform displayed on a screen of a display apparatus.

FIG. 5 depicts one example of a respiratory waveform displayed on a screen of a display apparatus.

FIG. 5 depicts one example of a respiratory waveform together with an electrocardiogram. In the electrocardiogram (labeled as "ECG"), the vertical axis represents voltage in mV and the horizontal axis represents time in seconds. In the respiratory waveform (labeled as "RESP"), the vertical axis represents the respiratory volume in ml and the horizontal axis represents time in seconds.

The frequency of the respiratory waveform is lower than the frequency of the electrocardiogram, and is around 1 Hz for example.

Second Embodiment

Figure 6:
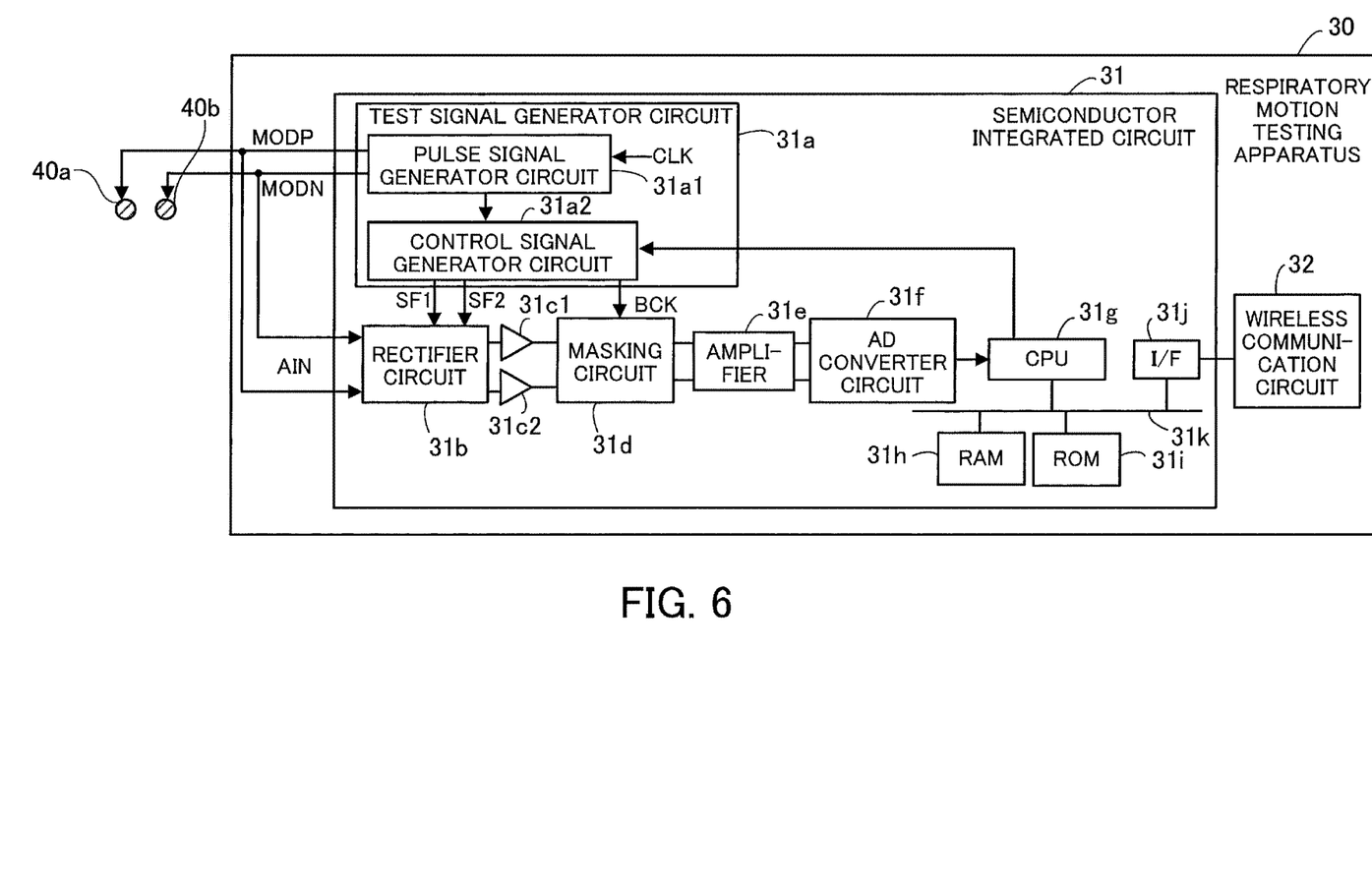
FIG. 6 depicts one example of a respiratory motion testing apparatus and a semiconductor integrated circuit according to a second embodiment.

FIG. 6 depicts one example of a respiratory motion testing apparatus and a semiconductor integrated circuit according to a second embodiment.

The respiratory motion testing apparatus 30 includes a semiconductor integrated circuit 31 and a wireless communication circuit 32.

The semiconductor integrated circuit 31 is a single-chip LSI, for example, and includes a test signal generator circuit 31a, a rectifier circuit 31b, buffers 31c1 and 31c2, a masking circuit 31d, an amplifier 31e, and an AD converter circuit 31f. The semiconductor integrated circuit 31 further includes a CPU 31g, a RAM 31h, a ROM 31i, an interface circuit (labeled as "I/F" in FIG. 6) 31j, and a bus 31k.

The test signal generator circuit 31a includes a pulse signal generator circuit 31a1 and a control signal generator circuit 31a2.

The pulse signal generator circuit 31a1 is equipped with the same functions as the pulse signal generator circuit 11a depicted in FIG. 1, and generates the pulse signal MODP to be supplied to an electrode 40a and the pulse signal MODN to be supplied to the electrode 40b. The electrodes 40a and 40b are placed on the chest of the subject. The pulse signal MODN is a signal whose phase differs to the pulse signal MODP by 180°.

The control signal generator circuit 31a2 is equipped with the same functions as the control signal generator circuit 11c depicted in FIG. 1. That is, using the control signals SF1 and SF2, the control signal generator circuit 31a2 causes the rectifier circuit 11b to invert the potential difference signal AIN to a positive voltage value from the timing at which the potential difference signal AIN becomes a negative voltage value.

In the semiconductor integrated circuit 31 according to the second embodiment, the control signal generator circuit 31a2 additionally generates a control signal BCK for controlling the masking circuit 31d. The timing of changes in the control signals SF1, SF2, and BCK is controlled by the CPU 31g.

Note that an example circuit configuration of the test signal generator circuit 31a will be described later.

The rectifier circuit 31b receives the potential difference signal AIN indicating the potential difference between the electrodes 40a and 40b and outputs a rectified signal produced by rectifying the potential difference signal AIN. The rectifier circuit 31b is realized by the same circuit as the rectifier circuit 11b depicted in FIG. 2.

The two input terminals of the masking circuit 31d are connected to two output terminals of the rectifier circuit 31b via the buffer 31c1 and the buffer 31c2, respectively. Note that the buffers 31c1 and 31c2 may be omitted. In a certain period that includes at least part of a transient response period of the rectified signal that occurs due to changes in the control signals SF1 and SF2, the masking circuit 31d holds and outputs the value of the rectified signal at the start of the certain period without the value being updated. In other words, the masking circuit 31d has a function of masking changes in the rectified signal during at least part of the transient response period of the rectified signal. The start timing of the masking period and the length of the period are decided by the control signal BCK.

The masking circuit 31d is realized by a sample and hold circuit, for example. One example of a sample and hold circuit is described later.

The amplifier 31e amplifies the rectified signal supplied via the masking circuit 31d.

The AD converter circuit 31f outputs a digital value based on the magnitude of the output signal of the masking circuit 31d. In the example in FIG. 6, the output signal (rectified signal) of the masking circuit 31d is amplified by the amplifier 31e and the output signal of the masking circuit 31d after amplification is converted to a digital value.

The CPU 31g loads a program and at least some of the data stored in the ROM 31i via the bus 31k into the RAM 31h and executes the program. As one example, by executing the program, the CPU 31g performs a process that calculates impedance based on the digital value outputted by the AD converter circuit 31f. As another example, by executing the program, the CPU 31g uses a relational expression for impedance and respiratory volume stored in advance in the ROM 31i to calculate a respiratory volume based on the calculated impedance. The CPU 31g may alternatively calculate the respiratory volume directly from the digital value outputted by the AD converter circuit 31f.

By executing a program, the CPU 31g also controls transmission and reception of information between the interface circuit 31j and the wireless communication circuit 32.

The RAM 31h is a volatile semiconductor memory that temporarily stores programs to be executed by the CPU 31g and data to be used in computation by the CPU 31g.

The ROM 31i is a nonvolatile storage apparatus that stores programs to be executed by the CPU 31g and various data.

The interface circuit 31j performs transmission and reception of information to and from the wireless communication circuit 32 under the control of the CPU 31g.

The wireless communication circuit 32 performs transmission and reception of information via wireless communication to and from an apparatus outside the respiratory motion testing apparatus 30 (for example, a tablet terminal). As one example, the wireless communication circuit 32 transmits information on the respiratory volume calculated by the CPU 31g to the external apparatus.

Figure 7:
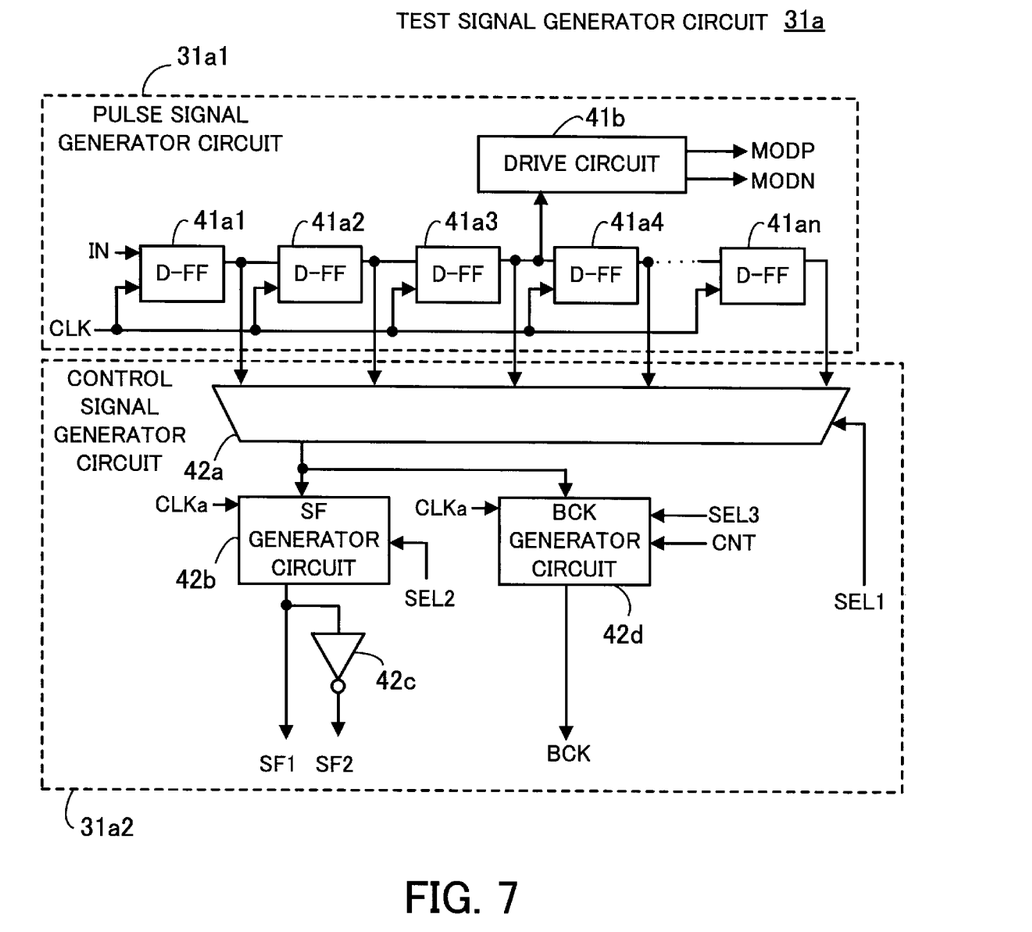
FIG. 7 depicts one example of a test signal generator circuit.

FIG. 7 depicts one example of a test signal generator circuit.

The pulse signal generator circuit 31a1 of the test signal generator circuit 31a includes D-type flip-flops (labeled "D-FF" in FIG. 7) 41a1, 41a2, 41a3, 41a4, . . . , 41an, and a drive circuit 41b.

The D-type flip-flops 41a1 to 41an are directly connected in n stages so that an output terminal of a preceding flip-flop is connected to the data input terminal of a following flip-flop, and are all supplied with a clock signal CLK.

Note that a signal IN produced by dividing the frequency of the clock signal CLK using a frequency divider circuit (not illustrated) by a predetermined division ratio is inputted into the data input terminal of the D-type flip-flop 41a1 that is the first stage. As one example, this frequency divider circuit divides the frequency of a 12 MHz clock signal CLK to generate a 32 KHz signal IN.

Signals that have been delayed by different delays (or shifts in phase) to the signal IN are outputted from each of the D-type flip-flops 41a1 to 41an. As one example, the signal outputted from the nth D-type flip-flop 41an has the largest delay compared to the signal IN.

The drive circuit 41b adjusts the signal IN that has been delayed by a predetermined delay to a predetermined voltage level, and generates and outputs the pulse signals MODP and MODN whose phase is 180° apart based on the signal whose voltage value has been adjusted. Although the drive circuit 41b is connected to the output terminal of the D-type flip-flop 41a3 in the example in FIG. 7, the drive circuit 41b may be connected to the output terminal of another D-type flip-flop.

The control signal generator circuit 31a2 includes a selector 42a, an SF generator circuit 42b, an inverter circuit 42c, and a BCK generator circuit 42d.

The selector 42a selects and outputs one output signal out of the D-type flip-flops 41a1 to 41an based on a selection signal SEL1 supplied from the CPU 31g.

The SF generator circuit 42b generates a plurality of signals by delaying the output signal of the selector 42a by different delays, selects one of the plurality of signals based on a selection signal SEL2 supplied from the CPU 31g, and outputs the selected signal as the control signal SF1.

The SF generator circuit 42b is realized using a shift register and a selector, for example. By using the shift register, a plurality of signals with different delays are obtained with the cycle of the clock signal CLKa as the resolution. Based on the selection signal SEL2, the selector selects one out of the plurality of signals with different delays and outputs the selected signal as the control signal SF1.

The clock signal CLKa is a signal with a frequency that is higher than (for example, around ten times higher than) the clock signal CLK. This means that it is possible to select the phase of the control signal SF1 with a more detailed resolution than the resolution of the phase of the output signal of the selector 42a.

The inverter circuit 42c outputs the control signal SF2 produced by inverting the phase of the control signal SF1 by 180°.

The selection signals SEL1 and SEL2 are set by the CPU 31g so that the control signals SF1 and SF2 change from the voltage VH to the voltage VL or from the voltage VL to the voltage VH at the timing of changes in the potential difference signal AIN.

The BCK generator circuit 42d generates a plurality of signals produced by delaying the output signal of the selector 42a by different delays and selects one out of the plurality of signals based on a selection signal SEL3 supplied from the CPU 31g. The BCK generator circuit 42d also adjusts the pulse width (duty ratio) of the selected signal based on a control signal CNT supplied from the CPU 31g and outputs the resulting signal as the control signal BCK. The selection signal SEL3 and the control signal CNT are set by the CPU 31g so that the control signal BCK becomes the voltage VL for a certain period that is at least part of the transient response period of the rectified signal that occurs due to changes in the control signals SF1 and SF2.

The BCK generator circuit 42d is realized using a shift register and a selector, for example. By using the shift register, a plurality of signals with different delays are obtained with the cycle of the clock signal CLKa as the resolution. Based on the selection signal SEL3 and the control signal CNT, the selector selects the rise timing and fall timing of the control signal BCK and outputs as the control signal BCK with an arbitrary delay and pulse width.

Figure 8:
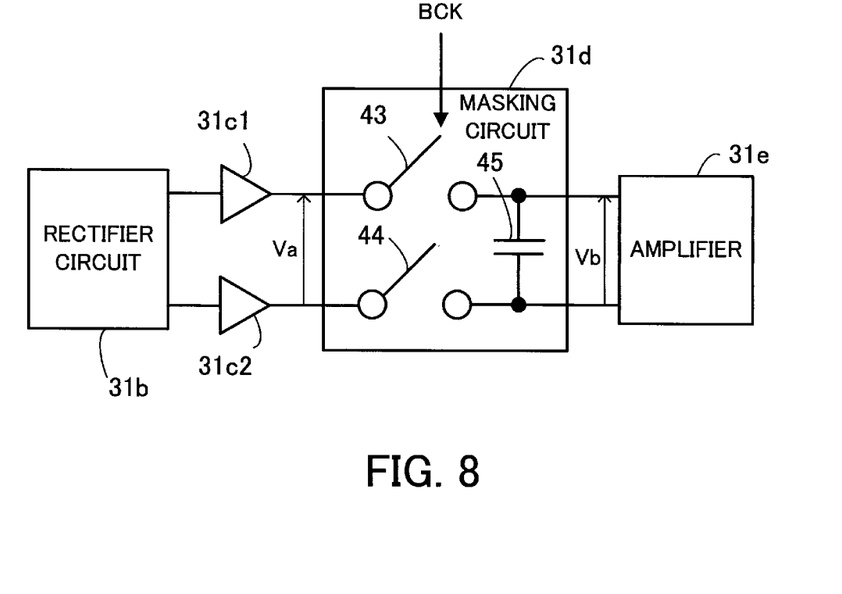
FIG. 8 depicts one example of a masking circuit.

FIG. 8 depicts one example of a masking circuit.

The masking circuit 31d includes switches 43 and 44 and a capacitor 45.

One end of the switch 43 is connected via the buffer 31c1 to one output terminal of the rectifier circuit 31b and another end of the switch 43 is connected to one input terminal of the amplifier 31e. One end of the switch 44 is connected via the buffer 31c2 to another output terminal of the rectifier circuit 31b and another end of the switch 44 is connected to another input terminal of the amplifier 31e. The switches 43 and 44 turn on or off based on the control signal BCK.

The switches 43 and 44 are realized by MOSFETs, for example. In the present embodiment, the control signal BCK is supplied to the gate electrodes of the MOSFETs and the MOSFETs are set in an on state or an off state in keeping with the voltage of the control signal BCK.

In the present embodiment, an example is described below where the switches 43 and 44 are turned on when the control signal BCK is the voltage VH and the switches 43 and 44 are turned off when the control signal BCK is the voltage VL.

The capacitor 45 is connected between the two input terminals of the amplifier 31e.

In the masking circuit 31d, when the control signal BCK becomes the voltage VH and the switches 43 and 44 are turned on, the output voltage Va of the rectifier circuit 31b is held by the capacitor 45. The output voltage Vb of the masking circuit 31d at this time becomes equal to the output voltage Va of the rectifier circuit 31b. On the other hand, when the control signal BCK becomes the voltage VL and the switches 43 and 44 are turned off, the output voltage Vb of the masking circuit 31d is the value held in the capacitor 45 regardless of any changes in the output voltage Va of the rectifier circuit 31b. That is, when the switches 43 and 44 are off, the changes in the output voltage Va are masked and not transmitted to the amplifier 31e and the AD converter circuit 31f that follows the amplifier 31e.

Example operations of the respiratory motion testing apparatus 30 and the semiconductor integrated circuit 31 according to the second embodiment will now be described.

Figure 9:
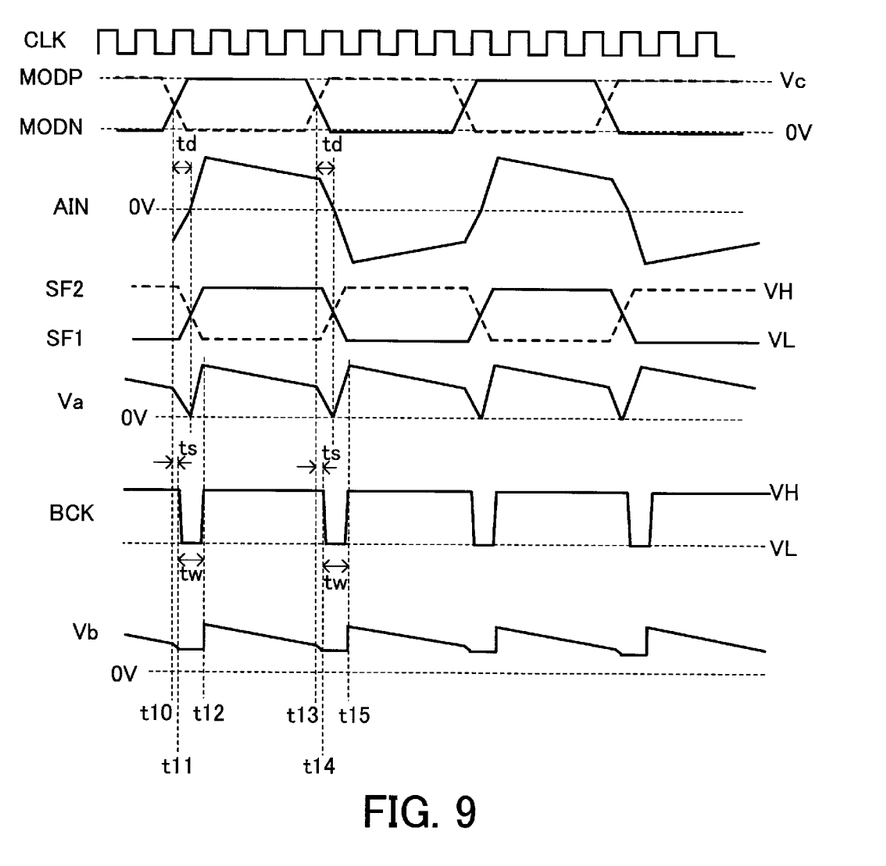
FIG. 9 is a timing chart depicting examples of signal waveforms of respective elements of the respiratory motion testing apparatus.

FIG. 9 is a timing chart depicting examples of signal waveforms of respective elements of the respiratory motion testing apparatus. In FIG. 9, examples of changes over time in the clock signal CLK, the pulse signals MODP and MODN, the potential difference signal AIN, the control signals SF1 and SF2, the output voltage Va of the rectifier circuit 31b, the control signal BCK, and the output voltage Vb of the masking circuit 31d are depicted.

In the same way as the respiratory motion testing apparatus 10 according to the first embodiment, the control signal generator circuit 31a2 changes the control signals SF1 and SF2 to the voltage VH or the voltage VL a time td after the timings t10 and t13 where the pulse signals MODP and MODN change. By doing so, as one example, the rectifier circuit 31b outputs the rectified signal, produced by inverting the potential difference signal AIN to a positive voltage value, starting from timing where the potential difference signal AIN becomes a negative voltage value, so that the output voltage Va of the masking circuit 31d is positive.

Accordingly, in the same way as the respiratory motion testing apparatus 10 according to the first embodiment, a period where the output voltage Va (which corresponds to the rectified signal DEMout of the rectifier circuit 11b in the first embodiment) becomes a negative voltage value is eradicated, so that rectification is performed properly and measurement errors for the impedance are avoided.

However, as depicted in FIG. 9, the output voltage Va has a high-frequency transient response component produced due to the changes in the control signals SF1 and SF2. For a configuration where the output voltage Va is directly supplied to the amplifier 31e, due to the influence of this high-frequency transient response component, there is the risk of the digital value after AD conversion not accurately reflecting the changes in impedance due to respiratory motion, which results in measurement errors for the impedance. This transient response component remains even when a simple smoothing process by a low pass filter or the like is performed at the AD converter circuit 31f.

With the respiratory motion testing apparatus 30 according to the second embodiment, the transient response component of the output voltage Va is cut as described below.

The control signal generator circuit 31a2 changes the control signal BCK from the voltage VH to the voltage VL at timings t11 and t14 a time is after the timings t10 and t13. By doing so, the switches 43 and 44 of the masking circuit 31d depicted in FIG. 8 become off, so that the value of the output voltage Va at timings t11 and t14 is held and becomes the output voltage Vb.

At timings t12 and t15 where a time equivalent to the pulse width tw of the control signal BCK set as described earlier has passed from the timings t11 and t14, the control signal BCK becomes the voltage VH. Due to this, the switches 43 and 44 of the masking circuit 31d depicted in FIG. 8 are turned on and the output voltage Vb becomes the same as the output voltage Va.

According to the processing described above, changes in the output voltage Va are not transmitted to the AD converter circuit 31f during a certain period that is at least part of the transient response period of the output voltage Va (corresponding to the transient response period of the rectified signal) that is produced due to the changes in the control signals SF1 and SF2. By doing so, there is a reduction in high-frequency transient response components in the output voltage Va that are transmitted to the AD converter circuit 31f and the input voltage of the AD converter circuit 31f is smoothed more effectively. This means that the error in the average voltage during a time period after AD conversion is reduced, measurement errors for impedance are suppressed, and it is possible to test respiratory motion more precisely.

Note that the timing (mask start timing) at which the control signal BCK changes from the voltage VH to the voltage VL may be earlier than the timing (the timings t10, t13, and the like) of the transient response of the pulse signals MODP and MODN. In this case, as one example, the selector 42a depicted in FIG. 7 may select an output signal of one of the D-type flip-flops 41a1 and 41a2 according to the selection signal SELL The timing of changes in the potential difference signal AIN fluctuates according to a variety of conditions, such as the types of the electrodes 40a and 40b, the lengths and types of the cables that connect the electrodes 40a and 40b and the respiratory motion testing apparatus 30, and the circuit configuration of the semiconductor integrated circuit 31. As one example, when the cables become longer, the timing of changes in the potential difference signal AIN are delayed relative to the timing of changes in the pulse signals MODP and MODN (that is, the time td becomes longer). With the respiratory motion testing apparatus 30 according to the second embodiment, it is possible to control the timing of changes in the control signals SF1 and SF2 using the selection signals SEL1 and SEL2 depicted in FIG. 7. This means that it is possible to cope with fluctuations in the timing of changes in the potential difference signal AIN (that is, fluctuations in the time td).

As one example, before the respiratory motion testing apparatus 30 is shipped, combinations of values of the selection signals SEL1 and SEL2 that are appropriate for various conditions may be stored in advance in the ROM 31i. Combinations of values of the selection signals SEL1 and SEL2 that are appropriate for various conditions are decided for example by detecting the timing of changes in the potential difference signal AIN in the various conditions and setting the combinations of values so that the control signals SF1 and SF2 change at the detected timing. After shipping, a combination of values of the selection signals SEL1 and SEL2 that corresponds to the conditions during testing may be acquired by the CPU 31g from the ROM 31i and supplied to the control signal generator circuit 31a2. Information on at least some of the conditions may be transmitted from an external apparatus (for example, a tablet terminal) and the wireless communication circuit 32 may receive this information and supply the information via the interface circuit 31j to the CPU 31g.

The start timing and period of the transient response of the output voltage Va also fluctuate according to the various conditions described above. With the respiratory motion testing apparatus 30 according to the second embodiment, it is possible to change the start timing of a masking period where the control signal BCK is set at the voltage VL to mask changes in the transient response period of the output voltage Va and the length of the masking period (the pulsewidth tw) using the selection signals SEL1 to SEL3 and the control signal CNT in FIG. 7. This means that it is possible to cope with fluctuations in the start timing and the length of the transient response of the output voltage Va.

As one example, before the respiratory motion testing apparatus 30 is shipped, combinations of values of the selection signals SEL1, SEL2, and SEL3 and the control signal CNT that are appropriate for various conditions may be stored in advance in the ROM 31i. Combinations of values of the selection signals SEL1, SEL2, and SEL3 and the control signal CNT that are appropriate for various conditions are decided for example by detecting the transient response period of the output voltage Va in the various conditions and setting the combinations based on the detection results so as to mask changes in the output voltage Va in a certain period that is at least part of the transient response period. After shipping, a combination that corresponds to the conditions during testing may be acquired by the CPU 31g from the ROM 31i and supplied to the control signal generator circuit 31a2. Information on at least some of the conditions may be transmitted from an external apparatus and the wireless communication circuit 32 may receive the information and supply the information via the interface circuit 31j to the CPU 31g.

On confirming the respiratory waveform displayed on the screen of a tablet terminal that has received information relating to respiratory volume, the user may use an input interface such as a touch panel to input a change request for the selection signals SEL1 to SEL3 or the control signal CNT. When this happens, the wireless communication circuit 32 receives information relating to the inputted change request and the CPU 31g changes one of the selection signals SEL1 to SEL3 or the control signal CNT based on the received information.

Measurement errors for impedance are avoided when testing respiratory movements according to impedance pneumography.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A semiconductor integrated circuit comprising:
   a pulse signal generator circuit configured to generate a first pulse signal, which is supplied to a first electrode configured to be placed on a chest of a subject, and a second pulse signal, which is supplied to a second electrode configured to be placed on the chest of the subject, a phase of the second pulse signal differing by 180° to a phase of the first pulse signal;

a rectifier circuit configured to receive a potential difference signal, start rectifying the potential difference signal based on a first control signal, and output a rectified signal produced by rectifying the potential difference signal, the potential difference signal being a signal in which an impedance between the first electrode and the second electrode is reflected, the impedance between the first electrode and the second electrode changing according to respiratory motion of the subject, first timing of a change of the potential difference signal caused by the first pulse signal or the second pulse signal changing being delayed for a period of time from second timing at which the first pulse signal or the second pulse signal changes;

a control signal generator circuit configured to generate the first control signal delayed for the period of time with respect to the first pulse signal or the second pulse signal, cause the rectifier circuit to start rectifying by supplying the first control signal, and cause the rectifier circuit to invert the potential difference signal, which becomes a negative voltage value from the first timing, to a positive voltage value from the first timing;

an analog to digital (AD) converter circuit configured to output a digital value based on a magnitude of the rectified signal;

a masking circuit configured to hold and output, based on a second control signal outputted by the control signal generator circuit and during a certain period including at least part of a transient response period of the rectified signal caused by a change in the first control signal, a value of the rectified signal at start timing of the certain period without the value changing; and a control circuit configured to control the start timing at which the masking circuit holds the value of the rectified signal or control a length of the certain period in which the masking circuit holds the value of the rectified signal in keeping with conditions for testing the respiratory motion, wherein the AD converter circuit outputs the digital value based on a magnitude of the output signal of the masking circuit, the pulse signal generator circuit includes a plurality of flip-flop circuits connected in series and outputting a plurality of delay signals which are obtained by delaying a first signal, which is obtained by dividing a first clock signal by a predetermined frequency division ratio, by different delays, and the pulse signal generator circuit includes a drive circuit that generates the first pulse signal and the second pulse signal based on a first delay signal among the plurality of delay signals, and the control signal generator circuit includes a selector selecting a second delay signal from the plurality of delay signals based on a first selection signal, and the control signal generator circuit includes a generation circuit generating the first control signal based on a second signal which is obtained by further delaying the second delay signal by a first delay amount selected from a plurality of delay amounts based on a second selection signal.

2. The semiconductor integrated circuit according to claim 1, wherein the control circuit controls timing at which the first control signal changes so as to cause the rectifier circuit to invert the potential difference signal, which becomes a negative voltage value from the first timing, to a positive voltage value from the first timing in keeping with a change in the period of time due to conditions for testing the respiratory motion.

3. A respiratory motion testing apparatus comprising:

a semiconductor integrated circuit that includes:

a pulse signal generator circuit configured to generate a first pulse signal, which is supplied to a first electrode configured to be placed on a chest of a subject, and a second pulse signal, which is supplied to a second electrode configured to be placed on the chest of the subject, a phase of the second pulse signal differing by 180° to a phase of the first pulse signal;

a rectifier circuit configured to receive a potential difference signal, start rectifying the potential difference signal based on a first control signal, and outputs a rectified signal produced by rectifying the potential difference signal, the potential difference signal being a signal in which an impedance between the first electrode and the second electrode is reflected, the impedance between the first electrode and the second electrode changing according to respiratory motion of the subject, first timing of a change of the potential difference signal caused by the first pulse signal or the second pulse signal changing being delayed for a period of time from second timing at which the first pulse signal or the second pulse signal changes;

a control signal generator circuit configured to generate the first control signal delayed for the period of time with respect to the first pulse signal or the second pulse signal time, cause the rectifier circuit to start by supplying the first control signal, and cause the rectifier circuit to invert the potential difference signal, which becomes a negative voltage value from the first timing, to a positive voltage value from the first timing;

an AD converter circuit configured to output a digital value based on a magnitude of the rectified signal;

a masking circuit configured to hold and output, based on a second control signal outputted by the control signal generator circuit and during a certain period including at least part of a transient response period of the rectified signal caused by a change in the first control signal, a value of the rectified signal at start timing of the certain period without the value changing;

a control circuit configured to control the start timing at which the masking circuit holds the value of the rectified signal or control a length of the certain period in which the masking circuit holds the value of the rectified signal in keeping with conditions for testing the respiratory motion; and a communication processing circuit that transmits information based on the digital value, wherein the AD converter circuit outputs the digital value based on a magnitude of the output signal of the masking circuit, the pulse signal generator circuit includes a plurality of flip-flop circuits connected in series and outputting a plurality of delay signals which are obtained by delaying a first signal, which is obtained by dividing a first clock signal by a predetermined frequency division ratio, by different delays, and the pulse signal generator circuit includes a drive circuit that generates the first pulse signal and the second pulse signal based on a first delay signal among the plurality of delay signals, and the control signal generator circuit includes a selector selecting a second delay signal from the plurality of delay signals based on a first selection signal, and the control signal generator circuit includes a generation circuit generating the first control signal based on a second signal which is obtained by further delaying the second delay signal by a first delay amount selected from a plurality of delay amounts based on a second selection signal.

* * * * *